US008796210B2

(12) United States Patent
Jezek

(10) Patent No.: US 8,796,210 B2
(45) Date of Patent: Aug. 5, 2014

(54) STABLE FORMULATION OF GROWTH HORMONE COMPRISING LACTATE ANION

(75) Inventor: Jan Jezek, Wellingborough (GB)

(73) Assignee: Arecor Limited, Cambridge (GB)

(*) Notice: Subject to any disclaimer, the term of this patent is extended or adjusted under 35 U.S.C. 154(b) by 888 days.

(21) Appl. No.: 12/851,295

(22) Filed: Aug. 5, 2010

(65) Prior Publication Data
US 2011/0034898 A1  Feb. 10, 2011

Related U.S. Application Data

(63) Continuation of application No. PCT/GB2009/050868, filed on Jul. 16, 2009.

(30) Foreign Application Priority Data

Jul. 16, 2008 (GB) .................................. 0813004.9

(51) Int. Cl.
A61K 38/27 (2006.01)

(52) U.S. Cl.
USPC ....................................................... 514/11.4

(58) Field of Classification Search
None
See application file for complete search history.

(56) References Cited

U.S. PATENT DOCUMENTS

| 3,051,627 | A | 8/1962 | Bradford et al. |
| 4,476,118 | A | 10/1984 | Brange et al. |
| 5,763,394 | A | 6/1998 | O'Connor et al. |
| 6,150,331 | A | 11/2000 | Tatsumi et al. |
| 6,448,225 | B2 * | 9/2002 | O'Connor et al. ........... 514/11.3 |
| 6,506,874 | B1 | 1/2003 | Dubaquie et al. |
| 2005/0031549 | A1 | 2/2005 | Quay et al. |
| 2005/0272657 | A1 | 12/2005 | O'Connor et al. |
| 2009/0136538 | A1 | 5/2009 | Jezek |
| 2009/0148406 | A1 | 6/2009 | Jezek |
| 2010/0028372 | A1 | 2/2010 | Jezek |
| 2011/0033549 | A1 | 2/2011 | Jezek |

FOREIGN PATENT DOCUMENTS

| EP | 0 009 222 A2 | 4/1980 |
| EP | 0 072 581 A1 | 2/1983 |
| EP | 0 513 914 A1 | 11/1992 |
| EP | 0 884 053 A1 | 12/1998 |
| EP | 0 938 902 A1 | 9/1999 |
| EP | 1 314 437 A1 | 5/2003 |
| EP | 1 336 410 A1 | 8/2003 |
| EP | 1 506 786 A1 | 2/2005 |
| GB | 2 188 419 A | 9/1987 |
| WO | 9828007 A1 | 7/1998 |
| WO | 98/56406 A1 | 12/1998 |
| WO | 03/009869 A1 | 2/2003 |
| WO | 03/021258 A1 | 3/2003 |
| WO | 03/039485 A2 | 5/2003 |
| WO | 2004019861 A2 | 3/2004 |
| WO | 2007/003936 A1 | 1/2007 |
| WO | 2007/109221 A2 | 9/2007 |
| WO | 2007/135425 A1 | 11/2007 |
| WO | 2008066322 A1 | 6/2008 |
| WO | 2008/084237 A2 | 7/2008 |
| WO | 2009/064838 A1 | 5/2009 |
| WO | 2010/089522 A1 | 8/2010 |

OTHER PUBLICATIONS

International Search Report for PCT/GB2009/050867 dated Apr. 23, 2010.
Remmele, R. L., et al., "Interleukin-1 Receptor (IL-1R) Liquid Formulation Development Using Differential Scanning Calorimetry," Pharmaceutical Research, 15(2): 200-208 (1998).
Elcock, A.H., "Realistic Modeling of the Denatured States of Proteins Allows Accurate Calculations of the pH Dependence of Protein Stability," J. Mol. Biol., 294(4), 1051-1062 (1999).
Alexov, E., "Numerical calculations of the pH of maximal protein stability. The effect of the sequence composition and three-dimensional structure," Eur. J. Biochem., 271(1), 173-185 (2004).
Antosiewicz, J., et al., "Prediction of pH-dependent Properties of Proteins," J. Mol. Biol., 238(3) 415-436 (1994).
Nelson, D., et al., Lehninger Principles of Biochemistry, 3rd Edition, Worth Publishers, p. 118 (2000).
Wilson, C. J., et al., XP0091 03220, "Role of cofactors in metalloprotein folding," Quarterly Review of Biophysics, 37 (3/4): 285-314 (2004).
Smith, A. T., et al., "Expression of a Synthetic Gene for Horseradish Peroxidase C in *Escherichia coli* and Folding and Activation of the Recombinant Enzyme with Ca2+ and Heme*," The Journal of Biological Chemistry, 265(22): 13335-13343 (1990).
Shi, X., et al., "Overexpression, purification, and characterization of a recombinant secretary catalase from *Bacillus subtilis*," Biotechnol Lett, 30: 181-186 (2008).
International Search Report for PCT/GB2009/050868 dated Apr. 23, 2010.
Gwinn, W., et al., "Scalable purification of *Bacillus anthracis* protective antigen from *Escherichia coli*," Protein Expression and Purification, 45: 30-36 (2006).

* cited by examiner

*Primary Examiner* — Christine J Saoud
(74) *Attorney, Agent, or Firm* — Sterne, Kessler, Goldstein & Fox P.L.L.C.

(57) ABSTRACT

An aqueous composition comprising a therapeutic protein further characterized in that
(i) the pH of the composition is adjusted to be between about 5.9 and 6.3, preferably about 6.1;
(ii) the composition comprises at least one displaced buffer having a pKa within 1 to 3 pH units of the pH of the composition;
(iv) the osmolarity of the composition is between 150-500 mOsm/L.

27 Claims, No Drawings

STABLE FORMULATION OF GROWTH HORMONE COMPRISING LACTATE ANION

RELATED APPLICATION

This application is a continuation of International Application No. PCT/GB2009/050868, which designated the United States and was filed on Jul. 16, 2009, which claims priority under 35 U.S.C. §119 or 365 to United Kingdom Application No. 0813004.9, filed on Jul. 16, 2008. The entire teachings of the above applications are incorporated herein by reference.

FIELD OF THE INVENTION

This invention relates the stability of human growth hormone, particularly the stability of human growth hormone in high concentration aqueous liquid compositions for therapeutic applications.

BACKGROUND TO THE INVENTION

Human growth hormone (hGH) is a human-specific hormone secreted by the anterior pituitary gland. The hormone is critical to the normal growth of children and is also significantly involved in regulating metabolism in both children and adults. Recombinant hGH is used in replacement therapy to treat conditions which produce short stature either due to hGH deficiency or due to other causes, such as Turner syndrome, Prader-Willi syndrome or intrauterine growth retardation.

Aqueous liquid compositions of hGH are very convenient and particularly suitable for convenient administration of the hormone by a pre-filled syringe or an injection pen. Several stabilized aqueous compositions of hGH have been disclosed based on the surprising observation that the presence of phenolic preservatives, particularly phenol, has a beneficial effect on stability of aqueous hGH. EP0955062 and WO2004/004780 disclose aqueous formulations of human growth hormone comprising a phenolic preservative. Whilst a range of phenolic preservatives, such as m-cresol, phenol, benzyl alcohol or benzethonium chloride, can be used according to EP0955062, WO2004/004780 is limited to phenol. The use of phenol as a preservative is claimed in WO2004/004780 to have been surprisingly provided improved stability of formulations of high concentrations of human growth hormone. Such formulations have been found to have a good resistance to crystallisation, i.e. formation of soluble and insoluble aggregates, over time. The most preferred concentration of phenol both in EP0955062 and in WO2004/004780 is 2.5 mg/mL, i.e. about 27 mM.

Apart from the use of phenolic compounds to improve stability of hGH, several other disclosures have been made describing stabilized liquid compositions of hGH. WO2005/027960 discloses compositions of hGH in the presence of polyethylene glycol (typically used at 10 mg/mL). Such formulations were demonstrated to reduce aggregation of hGH induced by agitation. At a concentration of hGH of 5 mg/mL, the protective effect was better than that observed in the presence of Poloxamer 188, a commonly used detergent in therapeutic formulations. The presence of polyethylene glycol was also shown to reduce to some extent chemical damage, such as deamidation during storage at 2-8° C. and 25° C. US2007/0014818 discloses hGH compositions in the presence of 1,2-propylene glycol showing reduced rate of crystallization as assessed by visual inspection compared with control compositions in the absence of 1,2-propylene glycol.

The key degradation pathways during storage of hGH, especially in aqueous liquid formulations, are deamidation and aggregation. The rate of deamidation is not significantly dependent on the concentration of the protein, and it can be minimized by keeping the pH of the formulation close to pH 6.1. The deamidation rate increases particularly at higher pH values wherein the alkaline deamidation process becomes prevalent. At lower pH values, it is a different mechanism of acidic deamidation which drives the conversion of amide groups of asparagine and glutamine to the respective carboxylic acids. The deamidated species of hGH are eqipotent with the native form of the protein and are not known to be more immunogenic than the native form. Nevertheless, the deamidation rate in the aqueous compositions of hGH should be kept at a minimum.

Whilst minimizing the rate of deamidation in therapeutic liquid compositions of hGH is of importance, it is critical to reduce the rate of aggregation processes. Formation of aggregates, both soluble and insoluble, increases significantly the risk of immunogenicity and strict limits are therefore imposed on the level of aggregates in such compositions. Aggregation is a process which is very dependent on the concentration of the protein. Consequently, aggregation is a particular problem in aqueous compositions comprising high concentration of hGH. Reducing the aggregation rate is therefore of particular importance in the case of high-concentration hGH compositions, such as compositions comprising >6 mg/mL and particularly >9 mg/mL of hGH.

The concentrations of hGH used in currently marketed liquid compositions are 3.3 mg/mL, 6.7 mg/mL or 10 mg/mL. It is very desirable to enable storage of such compositions at room temperature (<25° C.) at least for several days or ideally for several weeks. Whilst it is possible to ensure such stability at the lower end of the concentration range, the high rate of aggregation at the higher end of the concentration range (e.g., around 10 mg/mL) prevents the room temperature storage, even for a short period of time.

In order to receive regulatory approval for storage for a period of time at temperatures up to 25° C., it is essential to demonstrate acceptably low aggregation rate at 40° C. Accelerated stability trials at 40° C. are therefore a very important part of the stability assessment prior to approval. Typically, two parameters are used to assess acceptable aggregation rate in liquid formulations: (1) no particulate formation assessed either by eye or by a light scattering technique, and (2) <4% content of soluble high-molecular weight species (HMWS).

WO2007/003936 discloses stable compositions of proteins based on the presence of stabilizing agents characterized in that the one or more stabilizing agents have ionizable groups capable of exchanging protons with the protein, and the ionizable groups include first group that is positively charged when protonated and uncharged when deprotonated, and second group that is uncharged when protonated and negatively charged when deprotonated, the pKa of these ionizable groups being between 1 to 3 pH units from the pH of the composition.

WO2008/084237 describes how to improve, the stability of aqueous protein solutions. The disclosure is based on the discovery that buffers having a pKa at or near the pH of the solution are undesirable, when considering the protein's stability with respect to pH. Rather, the key to the invention is choice of the appropriate pH while minimizing the protein's ability to exchange hydrogen cations. In particular, an aqueous system is disclosed, which comprises a protein and one or more additives, characterized in that (i) the system is substantially free of a conventional buffer, i.e a compound with a pKa within 1 unit of the pH of the composition at the intended temperature range of storage of the composition;

(ii) the pH of the composition is set to a value at which the composition has maximum measurable stability with respect to pH;

(iii) the one or more additives (displaced buffers) are capable of exchanging protons with the protein and have pKa values at least 1 unit more or less than the pH of the composition at the intended temperature range of storage of the composition.

By keeping a protein at a suitable pH, at or near a value at which the measurable stability is maximal, in the absence of a conventional buffer, the storage stability of the protein can be increased substantially. Storage stability can generally be enhanced further, possibly substantially, by use of additives having pKa between 1 to 5 pH units, preferably between 1 to 3 pH units, most preferably between 1.5 to 2.5 pH units of the pH of the aqueous composition at the intended temperature range of storage of the composition. The presence of these additives also improves the pH stability of the formulation and is generally preferred.

SUMMARY OF THE INVENTION

The present invention discloses desirable formulation parameters which (independently or in combination) lead to improved stability, especially with respect to aggregate formation, in aqueous compositions. The present invention describes stable formulations of hGH for use in therapy, particularly formulations with reduced rates of aggregation. Stable aqueous compositions of hGH that manifest <1% aggregation after incubation at 40° C. for 8 weeks across a range of hGH concentrations are described. Formulations are particularly useful when formulating hGH at higher concentrations, such as more than 6 mg/ml and particularly around 10 mg/ml.

DESCRIPTION OF THE INVENTION

Deamidation of proteins in aqueous solutions is well known to those skilled in the art to proceed at slowest rate if the pH is adjusted to around 6.1. Such pH is therefore desirable in aqueous therapeutic formulations of proteins which exhibit deamidation as one of the degradation pathways. Human growth hormone is known to deamidate readily, so pH around 6.1 is optimal for its aqueous formulations. However, whilst it is important to ensure minimal deamidation rate by adjusting pH of the formulation, it is critical for therapeutic aqueous compositions of hGH to ensure minimal aggregation. The aggregation rate must be low across a conveniently useable hGH concentration range of hGH, such as between 3 mg/mL to 15 mg/ml, preferably between 6 mg/mL to 12 mg/mL, most preferably around 10 mg/mL. Formation of visible aggregates in such formulations at temperatures up to 40° C. for 8 weeks is to be avoided. In addition, there must be a low rate of HMWS formation such as <5%, preferably <2%, most preferably <1% after incubation at temperatures up to 40° C. for 8 weeks. Such low aggregation rates can be achieved in compositions disclosed herein.

In order to make an aqueous composition suitable for therapeutic application, particularly for subcutaneous application, certain desirable characteristics of the composition must be ensured, such as safety and regulatory acceptance of the excipients, and optimal osmolarity of the composition for the intended route of administration. The key compositions disclosed herein are based on excipients already approved by regulatory authorities as inactive ingredients in drug products. Preferred compositions optimize osmolarity for subcutaneous injection, e.g. around 300 mOsm/L. However, the invention is not limited to compositions having optimal osmolarity for subcutaneous administration.

A liquid composition for injection must be sterile. Sterility of a liquid composition for therapeutic use can be achieved by filtering the composition prior to the final filling to an appropriate container, such as a vial or a pre-filled syringe, under sterile conditions, using an appropriate filter or membrane, such as a 0.22 μm filter. In addition, compositions for multi-dose applications often require the presence of a preservative to ensure sterility beyond their first use. A number of chemicals have been approved for use in therapeutic compositions as preservatives. The phenolic compounds, such as phenol, m-cresol or benzyl alcohol are currently the most commonly used preservatives.

In contrast to the results reported in EP0955062 and WO2004/004780, new results indicate that the presence of phenol or m-cresol at concentrations around 30 mM (a typical concentration) increased significantly the rate of aggregation in aqueous compositions of hGH, particularly at ambient and elevated temperatures. The compositions according to the present invention can be used both in the presence and in the absence of such preservatives.

It was shown in the experimental work supporting the present invention that the nature of the buffering species is very important for the stability of proteins at a particular pH, especially with respect to minimizing the aggregation rate of the protein. In particular, it was shown that the use of compounds having pKa more than 1 unit from the pH of the formulation as the dominant buffering species to maintain the desired pH is beneficial for the stability of the protein. The use of such compounds is therefore desirable to improve stability of therapeutic proteins. However, since the species having pKa more than 1 unit from the pH of the formulation possess only a limited buffering capacity, it is beneficial to:

(1) ensure that the pKa of the buffering species is not too remote from the pH of the composition, being no more than 3 pH units, preferably no more than 2.5 pH units and most preferably no more than 2 pH unit from the pH of the composition;

(2) ensure that the concentration of such buffering species is relatively high in order to increase their buffering capacity, such as higher than 20 mM, preferably higher than 40 mM and most preferably higher than 60 mM.

(3) use two such species possessing between them a pKa more than 1 unit higher and a pKa more than 1 unit lower than the pH of the composition to ensure improved buffering capacity both on the alkaline and on the acidic side of the desired pH.

The term "displaced buffer" is used herein to encompass any additive present in a composition of specified pH which is capable of exchanging protons and has pKa value(s) at least 1 unit more or less than the pH of the composition at the intended temperature range of storage of the composition. The art of applying displaced buffers to formulations of biologicals is described in WO2008/084237, which is incorporated herein by reference. In the context of this invention, the term "displaced buffer" includes compounds with pKa between 1 to 3 pH units, preferably between 1 to 2.5 pH units, most preferably between 1 to 2 pH units from the pH of the composition.

The use of compounds having a pKa more than 1 unit from the pH as the dominant buffering species in compositions of therapeutic proteins is very unconventional and, in many respects, contradicts the conventional teaching of the practical use of pH buffers. Such buffering species are preferably used in formulations which are substantially free of conventional buffers, i.e., components having pKa within 1 unit from the pH of the formulation.

In order to make an aqueous composition suitable for therapeutic application, particularly for subcutaneous, intramuscular or intravenous application, it is preferred to select an osmolarity between 150-500 mOsm/L, preferably between 220-380 mOsm/L, most preferably around 300 mOsm/L. The osmolarity can be adjusted by addition of inactive species approved for use by the indicated route of delivery. Sodium chloride, amino acids or sugar alcohols such as mannitol can be used to adjust osmolarity to the desired concentration. However, the osmolarity can also be adjusted by increasing the concentration of the pH buffering species present in the composition.

The present invention includes an optionally sterile aqueous composition comprising hGH (or other therapeutic protein) further characterized in that:
(i) the pH of the composition is adjusted to a value around 6.1;
(ii) the composition comprises at least one displaced buffer having a pKa within 1 to 3 pH units of the pH of the composition;
(iii) the osmolarity of the composition is between 150-500 mOsm/L, preferably between 220-80 mOsm/L, most preferably around 300 mOsm/L.

The composition is preferably substantially free of conventional buffers, i.e. compounds having pKa within 1 pH unit of the pH of the formulation. One skilled in the art will appreciate that in the context of the present invention a pH around 6.1 means a pH range within which the rates of major degradation processes are not considerably different from those measurable at pH 6.1, preferably a pH range between 5.5 to 6.7, most preferably 5.8 to 6.4.

The present invention also includes an optionally sterile, aqueous composition comprising human growth hormone (or other therapeutic protein) at a concentration between 1 to 25 mg/mL, typically between 3 to 15 mg/mL, further characterized in that:
(i) the pH of the composition is adjusted to a value around 6.1;
(ii) the composition comprises at least one displaced buffer having a pKa within 1 to 3 pH units of the pH of the composition; and, optionally
(iii) the osmolarity of the composition is between 150-500 mOsm/L, preferably between 220-380 mOsm/L, most preferably around 300 mOsm/L. The composition is preferably substantially free of conventional buffers.

Surfactants are commonly used excipients in many approved therapeutic compositions of protein drugs. The presence of surfactants decreases the surface tension of the solvent, and thus reduces the rate of protein denaturation events at the liquid/gas interface. The presence of surfactants is therefore particularly important in minimizing protein denaturation due to sheer forces. In addition, surfactants may reduce the protein losses due to adsorption onto the walls of the containers. The most commonly used surfactants in therapeutic compositions are polysorbates (e.g. polysorbate 20, polysorbate 40, polysorbate 60 or polysorbate 80) or poloxamers (e.g. poloxamer 188 or poloxamer 407). Surfactants are typically used in compositions for therapeutic applications at concentrations between 0.002 to 0.5% (w/w).

The presence of surfactants may be beneficial, especially with respect to protein denaturation or protein aggregation due to sheer forces. Therefore, the invention provides an aqueous composition comprising human growth hormone (or other therapeutic protein) at a concentration between 1 to 25 mg/mL, typically between 3 to 15 mg/mL, further characterized in that:
(i) the pH of the composition is adjusted to a value around 6.1;
(ii) the composition is sterile;
(iii) the composition comprises at least one displaced buffer having a pKa within 1 to 3 pH units of the pH of the composition;
(iv) the osmolarity of the composition is between 150-500 mOsm/L, preferably between 220-380 mOsm/L, most preferably around 300 mOsm/L;
(v) the composition comprising a surfactant approved for use in drug products, such as polysorbate 20, polysorbate 40, polysorbate 60 or polysorbate 80, poloxamer 188 or poloxamer 407.

The composition is preferably substantially free of conventional buffers, i.e. compounds having pKa within 1 pH unit of the pH of the formulation.

Therapeutic compositions for multi-dose applications preferably comprise a preservative to ensure sterility beyond their first use. A number of chemicals have been approved for use in therapeutic compositions as preservatives. Phenolic compounds, such as phenol, m-cresol or benzyl alcohol are the most commonly used preservatives in drug products. The presence of such compounds in the stabilizing compositions disclosed herein was found to have a slight destabilizing effect causing increase in the aggregation rate of hGH. This is in direct contrast with stabilizing compositions of hGH disclosed previously (EP0955062 and WO2004/004780). Therefore, if possible, the aqueous compositions of hGH disclosed herein are preferably used in the absence of such phenolic preservatives to achieve maximal stabilizing effect. However, for multi-dose applications, which require the presence of a preservative the phenolic preservatives, can still be used in combination with the formulations disclosed herein. Whilst this will lead to a slight impairment of the stability of the therapeutic protein the final formulation will still show superior stability, particularly with respect to aggregation, over that observed in conventional formulations.

The native tertiary structure of hGH does not rely on the presence of a metal cation. No metal cations are therefore required in the formulation of hGH to improve its stability. Since metal cations can promote metal-facilitated aggregation of proteins it is beneficial to ensure their efficient removal from the formulation of hGH by adding ligands capable of forming strong co-ordinate bonds with metal cations. Consequently, aqueous compositions of hGH according to any aspect of the present invention can be used in the presence of a complexing agent such as EDTA or citrate anion.

It is particularly beneficial if one or more of the displaced buffers possess a metal-complexing ability. Such formulation does not require the presence of additional complexing agent to ensure efficient removal of metal cations. In this respect, a particularly useful displaced buffer for compositions around pH 6.1 is a lactate anion. Salts, such as a sodium or a potassium salt, of L-lactate or D-lactate or the mixture of the D- and the L-form can be used in therapeutic compositions according to the present invention. Alternatively, lactic acid (either D- or L-form) can be used as the ingredient in the compositions disclosed herein, with pH being adjusted by other excipients to the desired value.

Since the pKa of lactate is more than 1 unit lower than the optimal pH for storage of hGH (i.e. pH 6.1), it is beneficial to improve the buffering capacity of the formulation by using relatively high concentration of lactate anion, such as higher than 20 mM, preferably higher than 40 mM and most preferably higher than 60 mM. In addition, it is desirable to employ an additional displaced buffer having pKa more than 1 unit higher than the optimal pH for storage of hGH (i.e. pH 6.1) to ensure improved buffering capacity on the alkaline side of the desired pH. Tris(hydroxymethyl)aminomethane (TRIS) is a particularly useful additional displaced buffer to lactate anion.

In another embodiment, the present invention provides an optionally sterile aqueous composition comprising human growth hormone (or other therapeutic protein) at a concentration between 1 to 25 mg/mL, typically between 3 to 15 mg/mL, further characterized in that:
 (i) the pH of the composition is adjusted to a value around 6.1;
 (ii) the composition comprises a source of lactate anion;
 (iii) the osmolarity of the composition is between 150-500 mOsm/L, preferably between 220-380 mOsm/L, most preferably around 300 mOsm/L.

The composition is preferably substantially free of conventional buffers, i.e. compounds having pKa within 1 pH unit of the pH of the composition. The composition may additionally comprise one or more of the following:
 (iv) a source of TRIS;
 (v) a surfactant approved for use in drug products, such as polysorbate 20, polysorbate 40, polysorbate 60 or polysorbate 80, poloxamer 188 or poloxamer 407; and/or
 (vi) a preservative approved for use in drug products, such as phenol, m-cresol, benzyl alcohol, propylparaben, benzalkonium chloride and benzethonium chloride.

Since it is beneficial to use higher concentrations of lactate anion and TRIS to ensure sufficient buffering capacity at the desired pH of the composition, the most preferred embodiment of the present invention is an aqueous composition in which the required osmolarity is achieved mostly by these buffering species. So, the most preferred embodiment of the present invention is an aqueous composition comprising human growth hormone (or other therapeutic protein) at a concentration between 1 to 25 mg/mL, typically between 3 to 15 mg/mL, further characterized in that:
 (i) the pH of the composition is adjusted to a value around 6.1;
 (ii) the composition is sterile;
 (iii) the composition comprises a source of lactate anion and a source of TRIS used at concentrations ensuring the combined osmolarity, including counterions of these ingredients, between 150-500 mOsm/L, preferably between 220-380 mOsm/L, most preferably around 300 mOsm/L.

The composition is preferably substantially free of conventional buffers, i.e. compounds having pKa within 1 pH unit of the pH of the formulation. The composition may additionally comprise one or more of the following:
 (iv) a surfactant approved for use in drug products, such as polysorbate 20, polysorbate 40, polysorbate 60 or polysorbate 80, poloxamer 188 or poloxamer 407.
 (v) a preservative approved for use in drug products, such as phenol, m-cresol, benzyl alcohol, propylparaben, benzalkonium chloride and benzethonium chloride.

According to the present invention, considerably reduced rate of aggregation of hGH can be achieved in formulations adjusted to pH around 6.1 comprising a source of lactate anion and tromethamine (TRIS) in the presence of a pharmacologically acceptable surfactant such as Tween 80 or Poloxamer 188. Such formulations do not show any signs of visible precipitation following incubation at 40° C. for 4 weeks. In addition, <1% of HMWS can be observed in such formulations following incubation at 40° C. for 4 weeks as measured by size-exclusion chromatography. Such formulations also do not show any sign of visible precipitation following incubation at 25° C. for 18 weeks, and <4% of HMWS can be observed after 25° C. for 18 weeks.

The present invention includes an aqueous composition comprising human growth hormone further characterized in that:
 (i) no visible precipitation can be observed following incubation at 40° C. for 4 weeks;
 (ii) <1% of HMWS can be observed in such formulations following incubation at 40° C. for 4 weeks as measured by size-exclusion chromatography.

The present invention also includes an aqueous composition comprising human growth hormone further characterized in that:
 (i) no visible precipitation can be observed following incubation at 40° C. for 4 weeks;
 (ii) <1% of HMWS can be observed in such formulations following incubation at 40° C. for 4 weeks as measured by size-exclusion chromatography;
 (iii) the composition comprises a source of lactate ion at a concentration between 1 mM to 200 mM and a source of TRIS at a concentration between 1 mM and 200 mM.

In addition, the present invention includes an aqueous composition comprising human growth hormone further characterized in that:
 (i) no visible precipitation can be observed following incubation at 25° C. for 18 weeks;
 (ii) <3% of HMWS can be observed in such formulations following incubation at 25° C. for 18 weeks as measured by size-exclusion chromatography.

Furthermore, the present invention includes an aqueous composition comprising human growth hormone further characterized in that:
 (i) no visible precipitation can be observed following incubation at 25° C. for 18 weeks;
 (ii) <3% of HMWS can be observed in such formulations following incubation at 25° C. for 18 weeks as measured by size-exclusion chromatography;
 (iii) the composition comprises a source of lactate ion at a concentration between 1 mM to 200 mM and a source of TRIS at a concentration between 1 mM and 200 mM.

Preferably, the composition according to all aspects of the present invention comprise a pharmacologically acceptable surfactant such as polysorbate 20, polysorbate 40, polysorbate 60, polysorbate 80, poloxamer 188 or poloxamer 407.

Preferably, the osmolarity of the composition according to all aspects of the present invention is between 150-500 mOsm/L, more preferably between 220-380 mOsm/L, most preferably around 300 mOsm/L.

Preferably, the composition according to all aspects of the present invention is sterile, the sterility being achieved by filtering the composition prior to the final filling to an appropriate container, such as a vial or a pre-filled syringe, under sterile conditions, using an appropriate filter or membrane, such as a 0.22 μm filter.

Preferably, the composition according to all aspects of the present invention further comprises a pharmacologically acceptable preservative, such as phenol, m-cresol or benzyl alcohol.

Lactic acid (either D- or L-form) or salts, such as a sodium or a potassium salt, of L-lactate or D-lactate or the mixture of the D- and the L-form can be used as the source of lactate ion. Either TRIS base or TRIS hydrochloride can be used as a source of TRIS. One skilled in the art will understand that various combinations of a source of lactate anion and a source of TRIS can be employed to achieve the desired osmolarity. One skilled in the art will also understand that the osmolarity of the final composition will depend on the dissociation state and the presence of counter-ions in the starting ingredients, as well as the fact that any amount of a strong acid (such as hydrochloric acid) or a strong base (such as sodium hydroxide) used to adjust the pH of the final formulation will contribute to the osmolarity of the formulation.

The term "human growth hormone" is used herein to encompass a protein molecule produced by recombinant technology with amino acid sequence and biological activity identical or similar to that of the native human growth hormone.

All pKa values and all pH values used as parameters of compositions and excipients referred to herein are those measured at 25° C. or the nearest possible temperature. If possible, the pKa values listed in D. R. Lide. Handbook of Chemistry and Physics. 79th Edition, CRC Press LLC, Boca Raton, 1998 are referred to in the present invention. The term "conventional buffer" is used herein to encompass any compound having pKa within one pH unit of pH of the composition in which it is applied.

One skilled in the art will appreciate that in the context of the present invention a pH around 6.1 means a pH range within which the rates of major degradation processes are not considerably different from those measurable at pH 6.1, preferably a pH range between 5.5 to 6.7, most preferably 5.8 to 6.4.

Examples of the combinations of excipients to achieve a mixture comprising lactate anion and TRIS cation with osmolarity around 300 mOsm/L are shown in Table 1. The concentrations stated in the Table 1 are of the indicated components in the final composition.

TABLE 1

Examples of combinations of excipients to achieve a mixture comprising lactate anion and TRIS cation with osmolarity around 300 mOsm/L.

| No. | Sodium lactate | Lactic acid | TRIS.HCl | TRIS base | Final pH adjustment |
|---|---|---|---|---|---|
| 1 | 75 mM | | 75 mM | | HCl or NaOH |
| 2 | 90 mM | | 60 mM | | HCl or NaOH |
| 3 | 105 mM | | 45 mM | | HCl or NaOH |
| 4 | 120 mM | | 30 mM | | HCl or NaOH |
| 5 | | 150 mM | | 150 mM | HCl or NaOH |
| 6 | | 150 mM | | 100 mM | NaOH |
| 7 | | 150 mM | | 60 mM | NaOH |
| 8 | | 150 mM | | 30 mM | NaOH |

The invention is illustrated in the following Example.

Example

Formation of HMWS Species in Aqueous Formulations of Human Growth Hormone (10 mg/mL)

Formation of HMWS was followed in aqueous solutions of hGH (10 mg/mL) using the following size-exclusion HPLC method: the mobile phase was prepared by mixing 97 parts (v/v) of 63 mM sodium phosphate (pH 7.0) with 3 parts (v/v) of propan-2-ol. The mobile phase was filtered prior to its use. The liquid chromatograph (Agilent 1100 series) was equipped with a 214 nm detector, guard column and a 7.8×300 mm BioSep SEC-S2000 column. The flow rate was maintained at 0.6 mL/min. 15 µL of aqueous samples of human growth hormone were injected. The percentage of HMWS was expressed as the ratio of the total area of all peaks with shorter elution time than the monomeric form of hGH versus the total peak area, ignoring peaks corresponding the excipients. The hGH solutions were incubated at specified temperatures and assessed for the presence of HMWS at specific timepoints. In addition, the samples were assessed by eye for signs of visible precipitation. All samples tested were adjusted to pH 6.1, i.e. the optimal pH for storage of hGH with respect to deamidation rate. The rate of aggregate formation at 40° C. is shown in Table 2. The formulations based on lactate or TRIS/lactate buffering system were shown to result in considerably lower aggregation rate compared with control formulations based on phosphate or histidine, i.e. the buffers used in currently marketed formulations of hGH. In addition, there were no signs of visible precipitation in the lactate/TRIS formulations, whereas all control formulations showed signs of precipitation after 4 weeks of incubation at 40° C. Interestingly, the presence of phenol (30 mM) appeared to increase the aggregation rate in the formulations based on TRIS and/or lactate dosplaced buffers. This is in direct contrast with the prior art (e.g. EP0955062 or WO2004/004780) disclosing phenolic preservatives such as phenol as stabilizers capable of improving the aggregation rate of human growth hormone. Importantly, even in the presence of phenol, the compositions disclosed herein, based on lactate or TRIS/lactate buffering system still provide superior stability compared with the currently marketed compositions of human growth hormone.

The rate of aggregate formation at 25° C. is shown in Table 3. The formulations based on lactate or TRIS/lactate buffering system were shown to result in considerably lower aggregation rate compared with control formulations based on phosphate or histidine. Similar to the observation made during the storage at 40° C., the presence of phenol preservative appeared to increase the aggregation rate in the formulations based on TRIS and/or lactate dosplaced buffers. Nevertheless, even in the presence of phenol, the compositions disclosed herein, based on lactate or TRIS/lactate buffering system still provide superior stability compared with the currently marketed compositions of human growth hormone.

TABLE 2

Rate of HMWS formation in aqueous compositions of hGH at 40° C. both in the presence and in the absence of a preservative (phenol) measured by size-exclusion chromatography. All formulations were adjusted to pH 6.1.

| Background solution | % HMWS (2 weeks) | % HMMS (4 weeks) | Visible precipitation (4 weeks) |
|---|---|---|---|
| Phosphate buffer (10 mM) Mannitol (30 mg/mL) Tween 80 (100 mg/L) | 20.1% | 44.6% | Yes |
| Phosphate buffer (10 mM) Mannitol (30 mg/mL) Poloxamer 188 (2 mg/L) | 24.9% | 47.2% | Yes |
| Phosphate buffer (10 mM) Mannitol (30 mg/mL) Tween 80 (100 mg/L) Phenol (30 mM) | 13.1% | 32.4% | Yes |
| Phosphate buffer (10 mM) Mannitol (30 mg/mL) Poloxamer 188 (2 mg/L) Phenol (30 mM) | 9.6% | 28.1% | Yes |
| Histidine (10 mM) Mannitol (30 mg/mL) Poloxamer 188 (3 mg/L) | 9.2% | 18.9% | Yes |
| Histidine (10 mM) | 9.6% | 17.8% | Yes |

TABLE 2-continued

Rate of HMWS formation in aqueous compositions of hGH at 40° C. both in the presence and in the absence of a preservative (phenol) measured by size-exclusion chromatography. All formulations were adjusted to pH 6.1.

| Background solution | % HMWS (2 weeks) | % HMMS (4 weeks) | Visible precipitation (4 weeks) |
|---|---|---|---|
| Mannitol (30 mg/mL) Poloxamer 188 (3 mg/L) Histidine (10 mM) | 7.4% | 16.4% | Yes |
| Mannitol (30 mg/mL) Poloxamer 188 (3 mg/L) Phenol (30 mM) Histidine (10 mM) | 7.1% | 14.1% | Yes |
| Mannitol (30 mg/mL) Poloxamer 188 (3 mg/L) Phenol (30 mM) Lactate (30 mM) TRIS (25 mM) NaCl (100 mM) Tween 80 (100 mg/L) | <1% | <1% | No |
| Lactate (90 mM) TRIS (45 mM) Tween 80 (100 mg/L) | <1% | <1% | No |
| Lactate (140 mM) Tween 80 (100 mg/L) | <1% | <1% | No |
| Lactate (30 mM) TRIS (25 mM) NaCl (100 mM) Poloxamer188 (2 g/L) | <1% | <1% | No |
| Lactate (90 mM) TRIS (45 mM) Poloxamer188 (2 g/L) | <1% | <1% | No |
| Lactate (140 mM) Poloxamer188 (2 g/L) | <1% | <1% | No |
| Lactate (30 mM) TRIS (25 mM) NaCl (100 mM) Tween 80 (100 mg/L) Phenol (30 mM) | 5.1% | 8.1% | No |
| Lactate (90 mM) TRIS (45 mM) Tween 80 (100 mg/L) Phenol (30 mM) | 3.1% | 8.9% | No |
| Lactate (140 mM) Tween 80 (100 mg/L) Phenol (30 mM) | 2.5% | 6.7% | No |
| Lactate (30 mM) TRIS (25 mM) NaCl (100 mM) Poloxamer188 (2 g/L) Phenol (30 mM) | 1.9% | 5.1% | No |
| Lactate (90 mM) TRIS (45 mM) Poloxamer188 (2 g/L) Phenol (30 mM) | 2.1% | 4.5% | No |
| Lactate (140 mM) Poloxamer188 (2 g/L) Phenol (30 mM) | <0.5% | 4% | No |

TABLE 3

Rate of HMWS formation in aqueous compositions of hGH at 25° C. both in the presence and in the absence of a preservative (phenol) measured by size-exclusion chromatography. All formulations were adjusted to pH 6.1.

| Background solution | % HMWS (18 weeks) | Visible precipitation (18 weeks) |
|---|---|---|
| Phosphate buffer (10 mM) Mannitol (30 mg/mL) Tween 80 (100 mg/L) | 4.9% | Yes |
| Phosphate buffer (10 mM) Mannitol (30 mg/mL) | 16.0% | Yes |

TABLE 3-continued

Rate of HMWS formation in aqueous compositions of hGH at 25° C. both in the presence and in the absence of a preservative (phenol) measured by size-exclusion chromatography. All formulations were adjusted to pH 6.1.

| Background solution | % HMWS (18 weeks) | Visible precipitation (18 weeks) |
|---|---|---|
| Tween 80 (100 mg/L) Phenol (30 mM) Histidine (10 mM) | 4.8% | Yes |
| Mannitol (30 mg/mL) Poloxamer 188 (3 mg/L) Histidine (10 mM) | 4.0% | Yes |
| Mannitol (30 mg/mL) Poloxamer 188 (3 mg/L) Phenol (30 mM) Lactate (30 mM) TRIS (25 mM) NaCl (100 mM) Tween 80 (100 mg/L) | 2.0% | No |
| Lactate (90 mM) TRIS (45 mM) Tween 80 (100 mg/L) | 3.3% | No |
| Lactate (140 mM) Tween 80 (100 mg/L) | 2.2% | No |
| Lactate (30 mM) TRIS (25 mM) NaCl (100 mM) Poloxamer188 (2 g/L) | 1.8% | No |
| Lactate (90 mM) TRIS (45 mM) Poloxamer188 (2 g/L) | 1.6% | No |
| Lactate (140 mM) Poloxamer188 (2 g/L) | 1.8% | No |
| Lactate (30 mM) TRIS (25 mM) NaCl (100 mM) Tween 80 (100 mg/L) Phenol (30 mM) | 5.8% | No |
| Lactate (90 mM) TRIS (45 mM) Tween 80 (100 mg/L) Phenol (30 mM) | 2.6% | No |
| Lactate (140 mM) Tween 80 (100 mg/L) Phenol (30 mM) | 2.5% | No |
| Lactate (30 mM) TRIS (25 mM) NaCl (100 mM) Poloxamer188 (2 g/L) Phenol (30 mM) | 4.1% | No |
| Lactate (90 mM) TRIS (45 mM) Poloxamer188 (2 g/L) Phenol (30 mM) | 2.4% | No |
| Lactate (140 mM) Poloxamer188 (2 g/L) Phenol (30 mM) | 3.9% | No |

The invention claimed is:

1. An aqueous composition comprising human growth hormone as a therapeutic protein characterized in that:
   (i) the pH of the composition is between about 5.9 and 6.3;
   (ii) the composition comprises at least one displaced buffer having a pKa within 1 to 3 pH units of the pH of the composition and wherein the at least one displaced buffer is lactate anion; and
   (iii) the osmolarity of the composition is between 150-500 mOsm/L.

2. A composition according to claim 1, wherein the osmolarity is between 220-380 mOsm/L.

3. A composition according to claim 1, wherein the osmolarity is around 300 mOsm/L.

4. A composition according to claim 1, wherein the human growth hormone is at a concentration of 3 to 15 mg/mL.

5. A composition according to claim 1, which further comprises a surfactant approved for use in drug products.

6. A composition according to claim 1, which further comprises a preservative approved for use in drug products.

7. A composition according to claim 6, wherein the preservative is selected from phenol, m-cresol, benzyl alcohol, propylparaben, benzalkonium chloride and benzethonium chloride.

8. A composition according to claim 1, which is substantially free of a compound selected from phenol, m-cresol, benzyl alcohol, propylparaben, benzalkonium chloride and benzethonium chloride.

9. A composition according to claim 1, which further comprises the displaced buffer TRIS.

10. A composition according to claim 1, which is substantially free of a conventional buffer having a pKa within 1 pH unit of the pH of the composition.

11. The aqueous composition of claim 1 wherein the displaced buffers comprise lactate anion and TRIS.

12. A composition according to claim 11, which further comprises a surfactant approved for use in drug products, a preservative approved for use in drug products, or both.

13. A composition according to claim 12, wherein the preservative is selected from phenol, m-cresol, benzyl alcohol, propylparaben, benzalkonium chloride and benzethonium chloride and the surfactant is selected from the group consisting of polysorbate 20, polysorbate 40, polysorbate 60, polysorbate 80, poloxamer 188 and poloxamer 407.

14. A composition according to claim 1, wherein the pH is about 6.1.

15. An aqueous composition comprising human growth hormone as a therapeutic protein, characterized in that:
   (i) the pH of the composition is between about 5.9 and 6.3;
   (ii) the composition comprises lactate anions;
   (iii) the composition comprises a preservative selected from phenol, m-cresol, benzyl alcohol, propylparaben, benzalkonium chloride and benzethonium chloride; and
   (iv) the osmolarity of the composition is between 150-500 mOsm/L.

16. An aqueous composition according to claim 15, wherein following incubation at 40° C. for 4 weeks no visible precipitation is observed in the composition and >95 of the monomeric form of human growth hormone is retained in the composition as measured by size-exclusion chromatography.

17. An aqueous composition according to claim 16, wherein >97% of the monomeric form of human growth hormone is retained in the composition following incubation as measured by size-exclusion chromatography.

18. An aqueous composition according to claim 16, wherein >99% of the monomeric form of human growth hormone is retained in the composition following incubation as measured by size-exclusion chromatography.

19. A composition according to claim 15, which further comprises TRIS.

20. A composition according to claim 19, wherein the concentration of lactate anion is between 1 mM to 200 mM and the concentration of TRIS is between 1 mM and 200 mM.

21. A composition according to claim 15, wherein the osmolarity is between 220 and 380 mOsm/L.

22. A composition according to claim 21, wherein the osmolarity is about 300 mOsm/L.

23. A composition according to claim 15, which further comprises a surfactant approved for use in drug products.

24. A composition according to claim 23, wherein the surfactant is selected from the group consisting of polysorbate 20, polysorbate 60, polysorbate 80, poloxamer 188 and poloxamer 407.

25. The aqueous composition of claim 15, wherein the concentration of human growth hormone is greater than 6 mg/mL.

26. The aqueous composition of claim 25, wherein the concentration of human growth hormone is around 10 mg/mL.

27. A composition according to claim 15, wherein the human growth hormone is at a concentration of 3 to 15 mg/mL.

* * * * *